US00PP10327P

United States Patent [19]

Avila

[11] Patent Number: Plant 10,327

[45] Date of Patent: Apr. 14, 1998

[54] 'MORNING LORD' PEACH TREE

[75] Inventor: Fernando C. Avila, Hanford, Calif.

[73] Assignees: Fredrick A. Avila, San Ramon; Jeffrey D. Avila, Mill Valley, both of Calif.

[21] Appl. No.: 695,903

[22] Filed: Aug. 8, 1996

[51] Int. Cl.[6] ..... A01H 5/00

[52] U.S. Cl. ..... Plt./43.2

[58] Field of Search ..... Plt./43.2

*Primary Examiner*—James R. Feyrer
*Attorney, Agent, or Firm*—Worrel & Worrel

[57] ABSTRACT

A new and distinct variety of peach tree which is somewhat remotely similar to the "O'Henry" peach tree (U.S. Plant Pat. No. 2,964), but from which it is distinguished in a number of respects including by producing fruit which are mature for harvesting and shipment approximately one week after the fruit produced by the "O'Henry" peach tree and wherein the fruit is of a very high quality having a mild, pleasant flavor, a relatively low acidity, a red blush skin coloration and a firm flesh.

1 Drawing Sheet

BACKGROUND OF THE NEW VARIETY

The present invention relates to a new and distinct variety of peach tree, which will hereinafter be denominated varietally as the "Morning Lord" peach tree, and, more particularly, to a peach tree which produces high quality freestone fruit, which are mature for commercial harvesting and shipment approximately August 13 to August 24 in the San Joaquin Valley of central California.

The development of new fruit varieties is dependent not only upon the success with which such new varieties can be bred or discovered, but also upon how fortutously the ripening dates of such new varieties corrolate with the ripening dates of existing varieties. In addition, such considerations as fruit size, coloration, flavor, productivity and the like are also of importance. These considerations are particularly of significance in the case of new varieties of peach trees because of the great numbers of peach varieties available.

One of the more successful peach varieties over the years has been the O'Henry peach tree (U.S. Plant Pat. No. 2,964). This is perhaps the most popular variety of peach tree ripening in early to middle August in the San Joaquin Valley of central California. A new peach variety ripening near the same time in the growing season and possessing perhaps better attributes relative to such criteria, for example, as size, coloration and flavor would potentially be a good candidate for commercial success. The new variety of the subject invention appears to be such a variety.

ORIGIN AND ASEXUAL REPRODUCTION OF THE NEW VARIETY

The present variety of peach tree hereof was discovered by the inventor in about 1983 as a newly found seedling in his orchard which is located near Hanford in the San Joaquin Valley of central California. This parent tree was first asexually reproduced at the inventor's direction in 1991 on "Nemaguard" peach rootstock. The asexually reproduced trees were planted in 1991 near Hanford in the San Joaquin Valley of central California. The inventor has continually observed the asexually reproduced trees since that time and has found them to be in all respects identical to the parent tree.

SUMMARY OF THE NEW VARIETY

The "Morning Lord" peach tree is characterized by producing a late maturing, high quality freestone fruit having good fruit size and productivity. The fruit is highly colored, having a dark red skin coloration, and is ripe for commercial harvesting and shipment approximately August 13 to August 24 in the San Joaquin Valley of central California. The new variety is most closely similar to the "O'Henry" peach tree (U.S. Plant Pat. No. 2,964), but is distinguishable therefrom by the aforementioned ripening dates in that the new variety matures approximately one week after the fruit of the "O'Henry" peach tree. The new variety is further distinguishable therefrom by having a higher skin coloration in a range of from 10 percent to 20 percent. The fruit of the "O'Henry" peach tree is moderately acidic while the fruit of the new variety is much milder as a result of lower acidity. There is also a substantial difference in the bloom characteristics between the new variety and the "O'Henry" peach tree. The "O'Henry" peach tree has a normal flower petal count of five petals per flower. In contrast, the flowers of the new variety have up to as many as 20 petals per flower, making a very attractive floral display at bloom time in the spring.

BRIEF DESCRIPTION OF THE DRAWING

The accompanying drawing is a color photograph showing fruit of the new variety including a first in top plan view showing the stem cavity and shoulders thereof; a second in side elevation; a third in bottom plan view showing the apex thereof; a fourth in side elevation showing the suture thereof; a fifth sectioned and laid open to expose the stone thereof in its pit cavity in one section and the pit well in the other section; and representative foliage and wood all of the new variety.

DETAILED DESCRIPTION

Referring more specifically to the botanical details of this new and distinct variety of peach tree, the following has been observed under the ecological conditions prevailing at the orchard of origin which is located near Hanford, Calif. All major color code designations are by reference to the *Dictionary of Color*, by Maerz and Paul, First Edition. Common color names are also occasionally employed.

TREE

Generally:

*Size.*—The original tree ranges from 609.6 cm (20 feet) to 670.56 cm (22 feet) in width. Average tree height is 579.12 cm (19 feet), with 106.68 cm (3.5 feed to 152.4 cm (5 feet) of new growth.

*Vigor.*—Vigorous.

*General health.*—Hardy under typical climatic conditions in the San Joaquin Valley of California.

*Figure.*—Upright to upright-spreading in form. The tree is trained to an open vase pruning system.

*Productivity.*—Productive.

*Regularity of bearing.*—Regular.

Trunk:

*Size.*—152.4 mm (6 inches) from ground level, the trunk is 304.8 mm (12 inches) to 355.6 mm (14 inches) in diameter.

*Surface texture.*—Relatively coarse

*Color.*—Grey (7-C-7 Bonito Grey) to a darker grey (8-C-7).

*Lenticels.*—Large horizontally flattened lenticels and moderate scarfskin.

*Lenticels—form.*—Oval.

*Lenticels—size—length.*—5 mm (0.2 inches) to 12 mm (0.48 inches).

*Lenticels—size—height.*—2 mm (0.08 inches) to 4 mm (0.16 inches).

Branches:

*Size.*—Average in thickness.

*Surface texture.*—Ranges from smooth to slightly furrowed.

*Color—two year or older wood.*—Medium brown (7-E-11 Trotteur Tan).

*Color—immature branches.*—Pale green (20-J-4) with shoot areas exposed to direct sunlight often displaying a rose-red hue (5-F-9).

*Internode—length.*—Normal, from 29 mm (1.16 inches) to 40 mm (1.6 inches) between nodes on current season's hanger wood.

LEAVES

Size:

*Generally.*—Relatively large. The following measurements were taken from leaves growing on vigorous, upright, current season's shoots.

*Average length.*—Ranges from 18.7 cm (7.293 inches) to 23.1 cm (9.009 inches).

*Average width.*—Ranges from 4.3 cm (1.677 inches) to 5.1 cm (1.989 inches).

Thickness: Average.

Form: Lanceolate with an acuminate leaf tip.

Apex: Often slightly curled downwards and slightly twisted sideways.

Color:

*Upwardly disposed surface.*—Dark green (24-L-5).

*Downwardly disposed surface.*—Lighter grey-green (22-J-6).

*Leaf Vein.*—Lower midvein is prominent and pale green (19-I-5).

Marginal form:

*Generally.*—Crenate, with low, somewhat regular crenations.

Leaf margin: Slightly undulate.

Petiole:

*Size.*—Moderately long.

*Length.*—11 mm (0.44 inches) to 15 mm (0.6 inches).

*Thickness.*—Ranges from 2.0 mm (0.08 inches) to 2.5 mm (0.1 inches).

*Color.*—Light green (19-K-5) and darker green along the petiole groove.

Glandular characteristics: Medium to large in size.

Glands:

*Form.*—Variable with both reniform and globose forms present.

*Position.*—Alternate.

*Pattern.*—From 2 to 4 glands can often be present on the leaf petiole with an additional 2 to 3 glands present along the leaf blade margin basally. The petiole glands are most frequently stalked and mixed in form. The most basal 1 or 2 glands on the petiole are usually globose and the upper remaining glands are usually reniform. The glands along the basal leaf margin are almost always reniform.

*Color.*—Light, shiny green (18-L-6 Love Bird Green) when young, darkening with age.

Stipules: Small. The leaf stipules are early deciduous with very few remaining at the date of fruit maturity.

*Length.*—5 mm (0.2 inches) to 7 mm (0.28 inches).

*Form.*—Linear lanceolate with serrate margins.

*Color.*—Light green (20-K-3) initially, darkening and browning with age.

FLOWERS

Flower buds:

*Generally.*—The buds are slightly appressed to the bearing shoot and are hardy under typical San Joaquin Valley climatic conditions.

*Size.*—Medium.

*Surface texture.*—Very pubescent with long greyish colored pubescence.

*Form.*—Conic.

Flower bud scales:

*Color.*—Grey-brown (15-A-G Beaver Grey).

Flowers:

*Generally.*—Large and of the "Showy" type.

Date of bloom: Full bloom was Mar. 8, 1994. The bloom is average in relation to other peach cultivars.

Bloom quantity: Abundant.

Buds:

*Number.*—Per node varies from 1 to 3, but is most frequently 2 per node.

Size:

*Generally.*—Fully expanded, ranges from 39 mm (1.56 inches) to 49 mm (1.96 inches).

Flower petals:

*Generally—size.*—Variable, with multiple petals present.

*Generally—number.*—Total petal number from 15 to as many as 20.

*Generally—color.*—Young petals are light pink (1-E-7 Pink #4). Older petals darken to a rose-pink (1-B-4 Arbutus).

Outer whorl of petals:

*Number.*—5.

*Length.*—Large, from 20 mm (0.8 inches) to 23 mm (0.92 inches) each.

*Width.*—15 mm (0.6 inches) to 18 mm (0.72 inches) each.

*Form.*—Ovate.

*Petal claw.*—Short.

*Petal claw—form.*—Truncate.

*Petal claw—length.*—1.5 mm (0.06 inches) to 2.0 mm (0.08 inches).

*Petal claw—width.*—Averaging 1.5 mm (0.06 inches).

*Petal—margins.*—Moderately undulate with a generally rounded to slightly domed apex area.

Middle whorl of petals:
*Number.*—5.
*Size.*—Somewhat smaller than the outer whorl of petals.
*Petals—length.*—15 mm (0.6 inches) to 18 mm (0.72 inches).
*Width.*—13 mm (0.52 inches) to 15 mm (0.6 inches).
*Form.*—Narrowly ovate to oval.
*Petal claw—form.*—Longer and more tapered than of outer whorl.
*Petal claw—length.*—1.5 mm (0.06 inches) to 3.5 mm (0.14inches).
*Margins.*—Substantially undulate with a more domed apex.

Inner whorl of petals:
*Number.*—5 to 10.
*Size.*—Smaller than the petals of the outer and middle whorls and are highly irregular in size and form.
*Length.*—5 mm (0.2 inches) to 15 mm (0.6 inches).
*Width.*—4 mm (0.16 inches) to 14 mm (0.56 inches).
*Form.*—Oval to obovate.
*Petal claw—form.*—Long.
*Petal claw—length.*—5 mm (0.2 inches) to 8 mm (0.32 1 inches).
*Petal claw—width.*—1.0 mm (0.04 inches).
*Margins.*—Highly undulate or ruffled and the petals are often cupped inwards.

Pedicel:
*Size.*—Average.
*Length.*—From 2.5 mm (0.1 inches) to 3.0 mm (0.12 inches).
*Thickness.*—Averages 1.0 mm (0.04 inches).
*Surface.*—Glabrous.
*Color.*—Bright green (19-L-4).

Nectaries:
*Color.*—Bright orange (9-F-12), becoming somewhat dull with age.

Calyx:
*Surface.*—Glabrous.
*Color.*—Maroon (6-I-4), streaked with green (19-L-5 Cosse Green).

Sepal:
*Size.*—Average.
*Form.*—Ovate.
*Surface.*—Pubescent with a moderate amount of long greyish pubescence.
*Color.*—The exterior surfaces are maroon (6-J-3 Mineral Red) with greenish (19-L-5 Cosse Green) areas present, especially marginally.

Anthers:
*Size.*—Medium.
*Color.*—Tan (9-F-4) ventrally and red (5-L-11 Brickdust Red) dorsally.

Pollen: Abundant.
*Color.*—Yellow-gold (10-L-4 Light Chrome).

Stamen:
*Length.*—Varies from 8 mm (0.32 inches) to 14 mm (0.56 inches). The longest stamens are about equal in length to the pistil.

Filament:
*Color.*—Very light pink (1-B-7 Pink #1) when young, becoming dark rose (2-D-5) with maturity.

Pistil:
*Length.*—Ranges from 17 mm (0.68 inches ) to 19 mm (0.76 inches) including the ovary.
*Color.*—Light yellow-green (19-D-2 Reed Green).
*Surface.*—Somewhat variable, highly pubescent basally over the ovary and the base of the style, but nearly glabrous distally on the style near the stigma.

FRUIT

Maturity when described: The fruit is described in a firm condition at full maturity. Ripe for commercial harvesting and shipment in 1995 approximately August 13 to August 24 near Hanford, Calif. in the San Joaquin Valley of central California.

Size:
*Generally.*—Large and uniform.
*Average cheek diameter.*—Ranges from 75 mm (3. inches) to 87 mm (3.48 inches).
*Average diameter in suture plane.*—From 76 mm (3.04 inches ) to 89 mm (3.56 inches).
*Average diameter in axial plane.*—From 72 mm (2.88 inches) to 76 mm (3.04 inches).

Form:
*Uniformity.*—Somewhat variable from ovate to slightly oblate in lateral aspect and from globose to slightly oval in apical aspect.
*Symmetry.*—The fruit varies from asymmetrical to nearly symmetrical.

Suture:
*Generally.*—Relatively narrow line from 2 mm (0.08 inches) to 4 mm (0.16 inches) in width, extending from the base to the apex.
*Color.*—Can be variable, but is usually reddish (5-H-11 Moroccan Red) or blends with the underlying blush color. A slight amount of stitching can be present along the suture line. The suture is often, depressed on both sides of the apex, ventrally and dorsally, and often folded within the stem well.

Ventral surface:
*Generally.*—Relatively smooth, often with slight lipping on one side.

Stem cavity:
*Generally.*—Size—average.
*Width.*—Averaging from 28 mm (1.12 inches) to 35 mm (1.4 inches).
*Depth.*—11 mm (0.44 inches) to 17 mm (0.68 inches).
*Length.*—40 mm (1.6 inches) to 45 mm (1.8 inches).
*Form.*—Oval.
*Color.*—A yellow ground color stripe is often present over the basal shoulder where the bearing stem was pressed next to the fruit shoulder.

*Size.*—Average.
*Length.*—From 7 mm (0.28 inches) to 10 mm (0.4 inches).
*Thickess.*—From 3.0 mm (0.12 inches) to 3.5 mm (0.14 inches).
*Color.*—Pale green (13-K-2) to a green-brown (13-J-4).

Base:
*Form.*—Moderately truncate and most often very slightly oblique to the fruit axis.

Apex:
*Form.*—Variable, from rounded to slightly domed. The pistil point is most often slightly oblique and depressed within the apical suture.

Skin:
*Attachment.*—The skin is attached to the flesh at commercial maturity.
*Thickness.*—Average.
*Texture.*—The skin surface is lightly pubescent with a fine, short pubescence.

*Flavor.*—Relatively neutral.

*Tendency to crack.*—There has been no observed tendency for the skin to crack.

*Skin color.*—The skin is highly colored but variable, from 80% to 100% red blush. The blush pattern is in both washed and striped form throughout the fruit surface. The darkest blush areas are a dark red (6-J-11 Copperleaf) and the lighter colored surfaces are a red-orange (4-H-11 Samuri Red) with many shade variations in between.

Flesh:

*Flesh color.*—Yellow-gold (10-J-3 Amber Yellow) from the skin inwards towards the stone. Substantial red (4-K-10 Pepper Red) flecking is present in the flesh. The stone cavity is lined with dark red coloration, radiating outwards into the flesh fore 10 mm (0.4 inches) to 15 mm (0.6 inches).

*Stone cavity—color.*—Cavity color ranges from (4-K-11 Lacquer Red) to (5-L-11 Brickdust Red) to (6-K-10 Chalet Red). The red interior coloration becomes darker and more extensive with advancing maturity.

*Juice production.*—Juicy.

*Flavor.*—Mild, pleasant and relatively low in acidity.

*Aroma.*—Moderate in amount, pleasant.

*Texture.*—Firm with fine texture and somewhat crunchy at commercial maturity, becoming juicy after ripening.

*Ripening.*—Ripens evenly.

*Eating quality.*—Very good.

Stone:

*Attachment.*—A full freestone with some fiber attachment basally and within the lateral pits.

*Size.*—Medium. Length—ranges from 33 mm (1.32 inches) to 36 mm (1.44 inches). Width—26 mm (1.04 inches) to 30 mm (1.2 inches). Thickness—from 18 mm (0.72 inches) to 20 mm (0.8 inches).

*Form.*—Generally—variable, from oval to slightly obovate.

*Apex.*—Shape—raised with a short, dentate tip.

*Color.*—Dry—Medium brown (7-C-10 Kermanshah Brown). A moderate amount of purple stain is present on the stone surface.

*Base.*—Shape—broadly truncate. The base angle is most frequently oblique to the stone axis.

*Sides.*—Generally—vary from equal to slightly unequal.

*Surface.*—Irregular, heavily grooved and pitted.

*Ventral edge.*—Thickness—From 5 mm (0.2 inches) to 6 mm (0.24 inches) at mid-suture.

*Ventral wings.*—Moderately prominent. The most prominent from mid-suture towards the base.

*Dorsal edge.*—A deep groove is present along the dorsal edge, subtended by high, prominent ridges. The groove narrows and the ridges are somewhat eroded over the apical shoulder and next to the apex itself.

*Hilum.*—Large, oval and well defined with a thick, raised collar.

Although the new variety of peach tree possesses the described characteristics noted above as a result of the growing conditions prevailing near Hanford, Calif. in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by Plant Letters Patent is:

1. A new and distinct variety of peach tree substantially as illustrated and described which is somewhat remotely similar to the "O'Henry" peach tree (U.S. Plant Pat. No. 2,964), but from which it is distinguished in a number of 4 respects including by producing fruit which are mature for commercial harvesting and shipment approximately August 13 to August 24, or about one week after the "O'Henry" peach tree, in the San Joaquin Valley of central California and which has a high skin coloration.

* * * * *

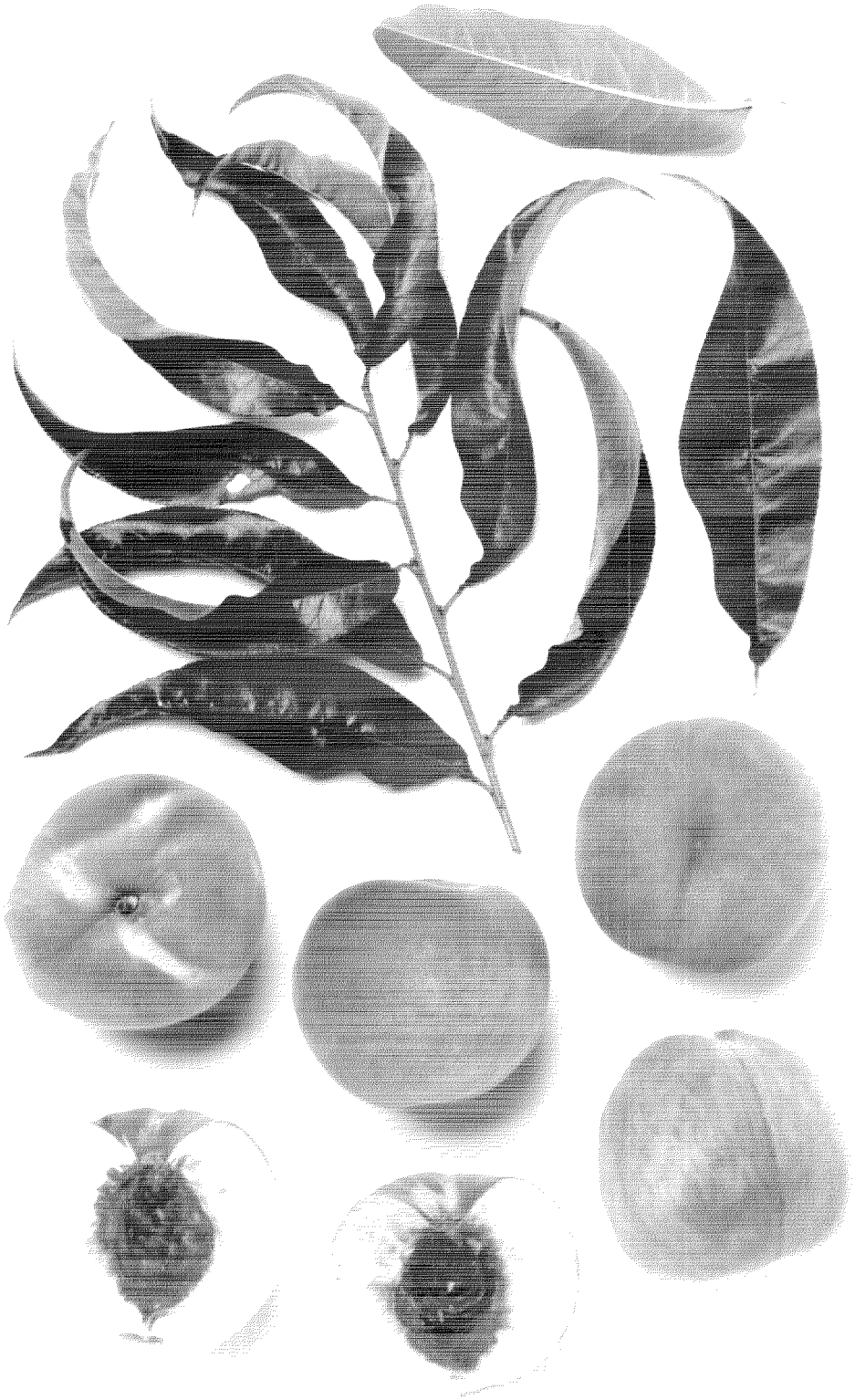

UNITED STATES PATENT AND TRADEMARK OFFICE

CERTIFICATE OF CORRECTION

PATENT NO. : PP10,327

DATED : April 14, 1998

INVENTOR(S) : FERNANDO C. AVILA

It is certified that error appears in the above-identified patent and that said Letters Patent is hereby corrected as shown below:

Column 3, line 1, delete "feed" and substitute ---feet---.

Column 3, line 56, delete "(19-I-5)" and substitute ---(19-J-5)---.

Column 7, Line 16, delete "fore" and substitute ---from---.

Column 8, line 35, delete "4".

Signed and Sealed this

Sixteenth Day of June, 1998

*Attest:*

*Attesting Officer*

Bruce Lehman

BRUCE LEHMAN

*Commissioner of Patents and Trademarks*